(12) United States Patent
Parthasaradhi Reddy et al.

(10) Patent No.: US 7,687,658 B2
(45) Date of Patent: Mar. 30, 2010

(54) PROCESS FOR OSELTAMIVIR PHOSPHATE

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Kesireddy Subash Chander Reddy, Hyderabad (IN)

(73) Assignee: Hetero Drugs Limited (IN)

( * ) Notice: Subject to any disclaimer, the term of this patent is extended or adjusted under 35 U.S.C. 154(b) by 186 days.

(21) Appl. No.: 11/718,359

(22) PCT Filed: Nov. 25, 2005

(86) PCT No.: PCT/IN2005/000381

§ 371 (c)(1),
(2), (4) Date: May 1, 2007

(87) PCT Pub. No.: WO2007/060681

PCT Pub. Date: May 31, 2007

(65) Prior Publication Data

US 2009/0054682 A1    Feb. 26, 2009

(51) Int. Cl.
*C07C 229/00*    (2006.01)
(52) U.S. Cl. ................................................ 560/125
(58) Field of Classification Search ................ None
See application file for complete search history.

(56) References Cited

FOREIGN PATENT DOCUMENTS

WO    98/07685    2/1998

OTHER PUBLICATIONS

Solomons, Organic Chemistry, 1992, 5th Edition, John Wiley & Sons, Inc., New York, pp. 786-788.*

* cited by examiner

*Primary Examiner*—Paul A Zucker
(74) *Attorney, Agent, or Firm*—Caesar, Rivise, Bernstein, Cohen & Pokotilow, Ltd.

(57) ABSTRACT

The present invention provides an improved and commercially viable process for the preparation of oseltamivir phosphate. Thus, for example, ethyl (3R,4R,5S)-4-amino-5-azido-3-(1-ethylpropoxy)-1-cyclohexene-1-carboxylate is acetylated with acetic anhydride in methylene chloride in the presence of triethyl amine in the absence of water to give ethyl (3R,4R,5S)-4-(acetylamino)-5-azido-3-(1-ethylpropoxy)-1-cyclohexene-1-carboxylate.

26 Claims, No Drawings

PROCESS FOR OSELTAMIVIR PHOSPHATE

FIELD OF THE INVENTION

The present invention provides an improved and commercially viable process for the preparation of oseltamivir phosphate.

BACKGROUND OF THE INVENTION

U.S. Pat. No. 5,763,483, which is herein incorporated by reference, disclosed carbocyclic compounds and pharmaceutically acceptable salts thereof. Among them Oseltamivir, chemically Ethyl (3R,4R,5S)-4-(acetylamino)-5-amino-3-(1-ethylpropoxy)-1-cyclohexene-1-carboxylate is a orally active inhibitor of influenza virus neuraminidase. Oseltamivir is represented by the following structure:

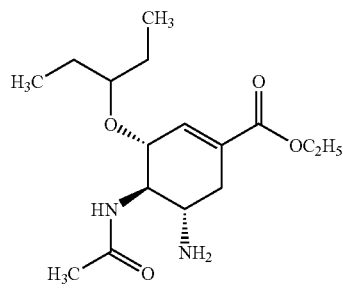

Various processes for preparation of oseltamivir were disclosed, for example, in U.S. Pat. No. 5,763,483, J. Org. Chem., Vol. 63, No. 13, 1998 (page: 4545-4550), J. Amer. Chem. Soc., Vol. 115, No. 4, 1997 (Page: 681-690), U.S. Pat. No. 5,952,375 and PCT Publication No. WO 99/44185.

In the preparation of oseltamivir, the compound of formula B:

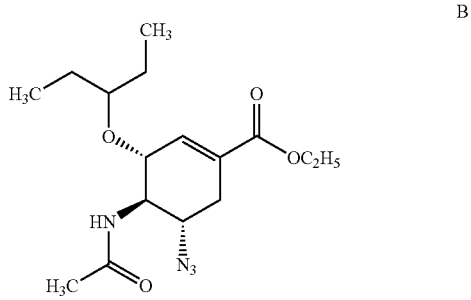

B is a key intermediate. According to the prior art processes, the intermediate of the formula B was prepared by acetylation of the compound of formula A:

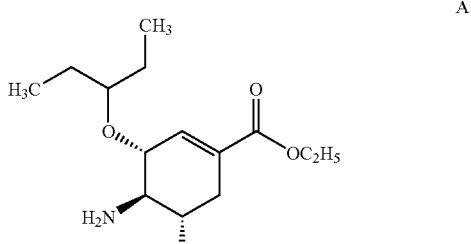

A with acetic anhydride in hexanes or methylene chloride in the presence of aqueous sodium bicarbonate; or with acetyl chloride and pyridine. The base such as sodium bicarbonate is normally used to convert the acetic acid formed as by-product into a water soluble salt such as sodium acetate and the salt formed is extracted into water present so as to move the equilibrium towards the formation of acetylated product of the formula B.

We have surprisingly found, in contrary to the prior art process and process normally followed, that acetylation reaction of compound of formula A proceeds with acetic anhydride in an organic solvent in the presence of an organic or inorganic base in the absence of water, cleanly to obtain acetyl derivative of the formula B in better purity and in better yield.

In the preparation of oseltamivir, the azide intermediate of formula B is reduced to the corresponding amine, (oseltamivir) of the formula C:

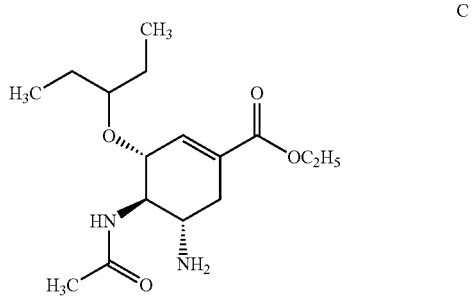

C

According to the prior art process, the reduction was carried out with hydrogen gas and a catalyst such as platinum on carbon or Lindlar's catalyst or reducing reagent such as trialkyl or triaryl phosphine.

We have found that the reduction of the compound of formula B to obtain the compound of formula C may be carried out using hydrogen sulfide or $Na_2S$ under suitable conditions in an advantageous manner.

DETAILED DESCRIPTION OF THE INVENTION

According to one aspect of the present invention, there is provided a process for preparing the acetyl compound of formula III:

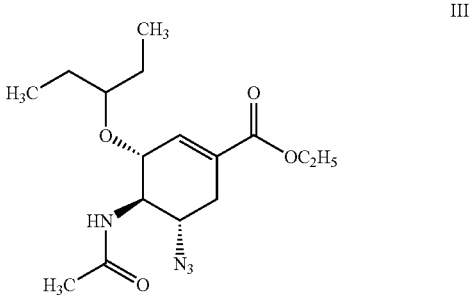

III which comprises acetylating the amino compound of formula II:

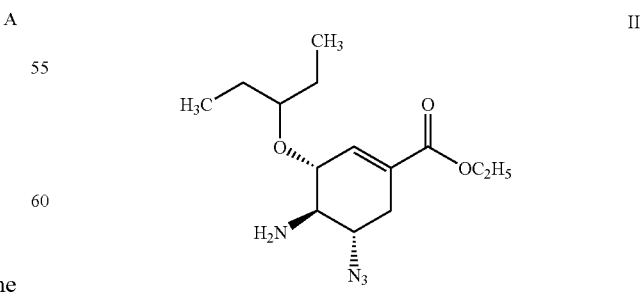

II with acetic anhydride in an organic solvent in the presence of an organic or inorganic base in the absence of water to give the acetyl compound of formula III. 'The absence of water' refers to the content of water in the reaction mass is less than 1.0%, preferably less than 0.5% and more preferably less than 0.2% of the reaction mass by volume.

Preferable organic base used in the reaction is an organic amine base such as triethyl amine, trimethyl amine, tributyl amine and n-butyl amine; and preferable inorganic base is selected from the group consisting of sodium bicarbonate and potassium bicarbonate. More preferable organic amine base is triethyl amine and more preferable inorganic base is sodium bicarbonate.

The reaction is preferably carried out at about 0-35° C., more preferably at about 10-30° C. and still more preferably at about 15-25° C.

Preferable organic solvent used in reaction is selected from chlorinated hydrocarbon solvents such as methylene chloride, ethylene dichloride and chloroform; hydrocarbon solvents such as n-hexane; and a mixture thereof. More preferable organic solvent is selected from methylene chloride, n-hexane and a mixture thereof. Most preferable organic solvent is methylene chloride.

After the reaction is completed, the reaction mass may then be subjected to usual work up such as washings, extractions etc.

According to another aspect of the present invention, there is provided a process for preparing the oseltamivir of formula I:

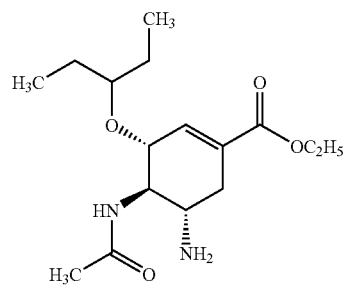

or a pharmaceutically acceptable salt thereof; which comprises reducing the compound of formula III:

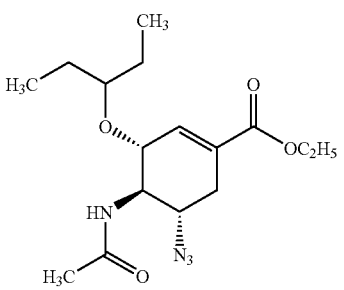

with hydrogen sulfide in presence of pyridine or ethanol or water or a mixture thereof; or with $Na_2S$ in presence of an organic amine base in an alcoholic solvent to give oseltamivir of formula I and optionally converting oseltamivir formed into a pharmaceutically acceptable acid addition salts of oseltamivir.

The reduction reaction is preferably carried out with hydrogen sulfide in presence of pyridine.

Preferable organic amine base used in the reduction reaction with $Na_2S$ is triethyl amine or trimethyl amine and more preferable organic amine base being triethyl amine. Preferable alcoholic solvent is methanol, ethanol or isopropyl alcohol and more preferable alcoholic solvent being methanol.

The reduction reaction is preferably carried out at about 0-45° C., more preferably at about 10-35° C. and still more preferably at about 20-35° C.

According to another aspect of the present invention, there is provided an improved process for preparing the oseltamivir of formula I:

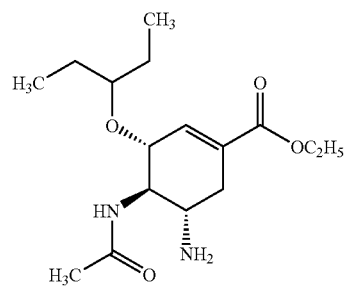

or a pharmaceutically acceptable salt thereof;

which comprises:

a) acetylating the amino compound of formula II:

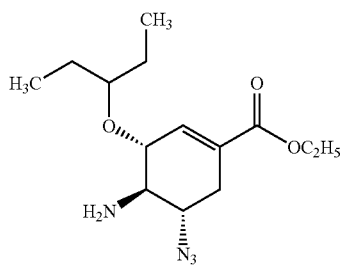

with acetic anhydride in an organic solvent in the presence of an organic or inorganic base in the absence of water to give the acetyl compound of formula III:

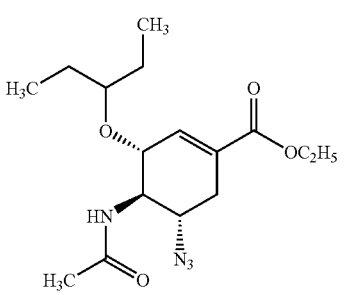

b) reducing the compound of formula III with hydrogen sulfide in presence of pyridine or ethanol or water or a mixture thereof; or with $Na_2S$ in presence of an organic amine base in an alcoholic solvent to give oseltamivir of formula I and optionally converting oseltamivir formed into a pharmaceutically acceptable acid addition salts of oseltamivir.

Preferable organic base used in step-(a) is an organic amine base such as triethyl amine, trimethyl amine, tributyl amine and n-butyl amine; and preferable inorganic base is selected from the group consisting of sodium bicarbonate and potassium bicarbonate. More preferable organic amine base is triethyl amine and more preferable inorganic base is sodium bicarbonate.

The reaction in step-(a) is preferably carried out at about 0-35° C., more preferably at about 10-30° C. and still more preferably at about 15-25° C.

Preferable organic solvent used in step-(a) is selected from chlorinated hydrocarbon solvents such as methylene chloride, ethylene dichloride and chloroform; hydrocarbon solvents such as n-hexane; and a mixture thereof. More preferable organic solvent is selected from methylene chloride, n-hexane and a mixture thereof. Most preferable organic solvent is methylene chloride.

The reaction in step-(b) is preferably carried out with hydrogen sulfide in presence of pyridine.

Preferable organic amine base used in the reaction with $Na_2S$ in step-(b) is triethyl amine or trimethyl amine and more preferable organic amine base being triethyl amine. Preferable alcoholic solvent used in the reaction in step-(b) is methanol, ethanol or isopropyl alcohol and more preferable alcoholic solvent being methanol.

The reaction in step-(b) is preferably carried out at about 0-45° C., more preferably at about 10-35° C. and still more preferably at about 20-35° C.

The invention will now be further described by the following non-limiting examples.

Example 1

Step-I

Ethyl (3R,4R,5S)-4-Amino-5-azido-3-(1-ethylpropoxy)-1-cyclohexene-1-carboxylate (14 gm) was added to triethyl amine (10 gm) and methylene chloride (110 ml) and then the contents were cooled to 20° C. To the contents added acetic anhydride (5.6 gm) at 20-25° C. for 1 hour and then stirred for 3 hours at 20-25° C. The reaction mass was quenched into water (140 ml) and then separated the layers. The organic layer was washed with 8% sodium bicarbonate solution (140 ml) and then washed with 30% sodium chloride solution (140 ml). The organic layer was distilled and recrystallized from n-hexane (70 ml) to give 8.5 gm of Ethyl (3R,4R,5S)-4-(Acetylamino)-5-azido-3-(1-ethylpropoxy)-1-cyclohexene-1-carboxylate.

Step-II

Ethyl (3R,4R,5S)-4-(Acetylamino)-5-azido-3-(1-ethylpropoxy)-1-cyclohexene-1-carboxylate (8.5 gm) was dissolved in tetrahydrofuran (130 ml) and then triphenyl phosphine (10.5 gm) and water (50 ml) are added. The contents were heated to reflux, refluxed for 5 hours and then distilled off the solvent under vacuum. To the reaction mass added ethyl acetate (80 ml), washed with 30% sodium chloride solution (50 ml) and distilled off the solvent completely under vacuum. Acetone (130 ml) was added to the residue, heated to reflux, under reflux the mixture of $H_3PO_4$ (3 gm) and ethyl acetate (50 ml) was slowly added during 1 hour and then refluxed for 1 hour. The reaction mass was cooled to 25° C. and stirred for 2 hours at 20-25° C. Filtered the solid, washed with acetone (10 ml) and dried at 60-65° C. for 4 hours to yield 6.5 gm of oseltamivir phosphate (HPLC Purity: 99.6%).

Example 2

Ethyl (3R,4R,5S)-4-(Acetylamino)-5-azido-3-(1-ethylpropoxy)-1-cyclohexene-1-carboxylate (8.5 gm) was added to pyridine (200 ml) and then bubbled $H_2S$ gas for 3 hours at 25-35° C. Stopped the bubbling of $H_2S$ gas and then the reaction mixture was stirred for 5 hours at 25-35° C. The reaction mass was flushed with $N_2$ gas for 20-30 minutes and distilled off the solvent completely under reduced pressure keeping the bath temperature below 50° C. To the residue added ethyl acetate (100 ml) and washed with 30% sodium chloride solution (50 ml). Distilled off the ethyl acetate completely under reduced pressure. Acetone (100 ml) was added to the residue, heated to reflux, under reflux the mixture of $H_3PO_4$ (3.2 gm) and ethanol (25 ml) was slowly added during 1 hour 30 minutes and then refluxed for 2 hours. The reaction mass was cooled to 25° C. and then stirred for 2 hours at 20-25° C. Filtered the solid, washed with acetone (10 ml) and dried at 60-65° C. for 4 hours to give 6.9 gm of oseltamivir phosphate (HPLC purity: 99.8%).

Without further elaboration of the foregoing will so fully illustrate our invention that others may, by applying current or future knowledge, adapt the same for use under various conditions of service.

We claim:

1. A process for the preparation of oseltamivir of the formula I:

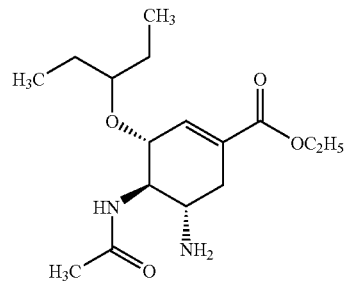

or a pharmaceutically acceptable salt thereof; which comprises reducing the compound of the formula III:

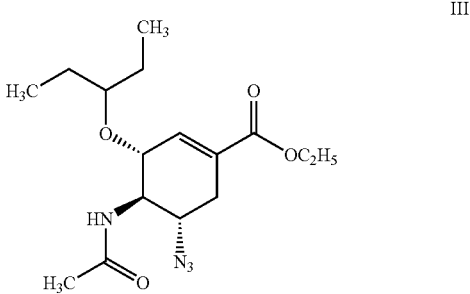

with hydrogen sulfide in the presence of pyridine or ethanol or water or a mixture thereof; or with $Na_2S$ in the presence of an organic amine base in an alcoholic solvent to give oseltamivir of the formula I and optionally converting oseltamivir formed into a pharmaceutically acceptable acid addition salt.

2. The process as claimed in claim 1, wherein the reaction is carried out with hydrogen sulfide in presence of pyridine.

3. The process as claimed in claim 1, wherein the organic amine base is triethyl amine or trimethyl amine.

4. The process as claimed in claim 3, where the organic amine base is triethyl amine.

5. The process as claimed in claim 1, wherein the alcoholic solvent is methanol, ethanol or isopropyl alcohol.

6. The process as claimed in claim 5, wherein the alcoholic solvent is methanol.

7. The process as claimed in claim 1, wherein the reaction is carried out at about 0-45° C.

8. The process as claimed in claim 7, wherein the reaction is carried out at about 10-35° C.

9. The process as claimed in claim 8, wherein the reaction is carried out at about 20-35° C.

10. A process for preparation of oseltamivir of the formula I:

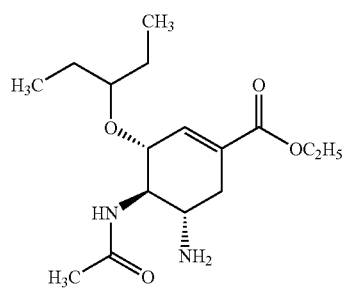

or a pharmaceutically acceptable salt thereof;
which comprises:
a) acetylating the amino compound of the formula II:

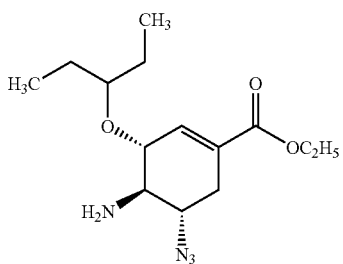

with acetic anhydride in an organic solvent in the presence of an organic or inorganic base in the absence of water to give the acetyl compound of the formula III:

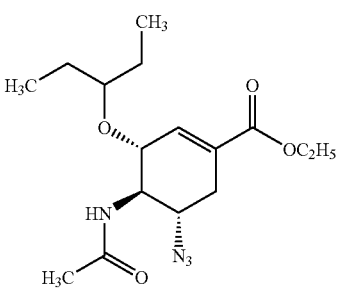

b) reducing the compound of the formula III with hydrogen sulfide in the presence of pyridine or ethanol or water or a mixture thereof; or with $Na_2S$ in the presence of an organic amine base in an alcoholic solvent to give oseltamivir of the formula I and optionally converting the oseltamivir formed into a pharmaceutically acceptable acid addition salt.

11. The process as claimed in claim 10, wherein the organic base used in step (a) is an organic amine base selected fom the group consisting of triethyl amine, trimethyl amine, tributyl amine and n-butyl amine; and the inorganic base is selected from the group consisting of sodium bicarbonate and potassium bicarbonate.

12. The process as claimed in claim 11, wherein the organic amine base is triethyl amine.

13. The process as claimed in claim 12, wherein the inorganic base is sodium bicarbonate.

14. The process as claimed in claim 10, wherein the acetylation reaction in step-(a) is carried out at about 0-35° C.

15. The process as claimed in claim 14, wherein the reaction is carried out at about 10-30° C.

16. The process as claimed in claim 15, wherein the reaction is carried out at about 15-25° C.

17. The process as claimed in claim 10, wherein the organic solvent used in step (a) is a solvent selected from the group consisting of methylene chloride, ethylene dichloride, chloroform, n-hexane; and a mixture thereof.

18. The process as claimed in claim 17, wherein the organic solvent is methylene chloride.

19. The process as claimed in claim 10, wherein reaction in step-(b) is carried out with hydrogen sulfide in presence of pyridine.

20. The process as claimed in claim 10, wherein the organic amine base used in the reaction in step-(b) is triethyl amine or trimethyl amine.

21. The process as claimed in claim 20, wherein the organic amine base is triethyl amine.

22. The process as claimed in claim 10, wherein the alcoholic solvent used in the reaction in step-(b) is methanol, ethanol or isopropyl alcohol.

23. The process as claimed in claim 22, wherein the alcoholic solvent is methanol.

24. The process as claimed in claim 10, wherein the reaction in step-(b) is carried out at about 0-45° C.

25. The process as claimed in claim 24, wherein the reaction is carried out at about 10-35° C.

26. The process as claimed in claim 25, wherein the reaction is carried out at about 20-35° C.

* * * * *